(12) United States Patent
Trennepohl

(10) Patent No.: US 8,246,596 B2
(45) Date of Patent: *Aug. 21, 2012

(54) ABSORBENT ARTICLE HAVING A MULTI-DIMENSIONALLY CONTOURED BARRIER CUFF

(75) Inventor: Michael Dale Trennepohl, Green Township, OH (US)

(73) Assignee: The Procter & Gamble Company, Cincinanti, OH (US)

( * ) Notice: Subject to any disclaimer, the term of this patent is extended or adjusted under 35 U.S.C. 154(b) by 213 days.

This patent is subject to a terminal disclaimer.

(21) Appl. No.: 12/651,672

(22) Filed: Jan. 4, 2010

(65) Prior Publication Data

US 2010/0106126 A1    Apr. 29, 2010

Related U.S. Application Data

(63) Continuation of application No. 11/400,467, filed on Apr. 7, 2006, now Pat. No. 7,666,175.

(51) Int. Cl.
  A61F 13/15 (2006.01)
  A61F 13/20 (2006.01)
(52) U.S. Cl. .......... 604/385.28; 604/385.01; 604/385.24
(58) Field of Classification Search ............. 604/385.01, 604/385.16, 385.21, 385.28
  See application file for complete search history.

(56) References Cited

U.S. PATENT DOCUMENTS

| | | |
|---|---|---|
| 3,860,003 A | 1/1975 | Buell |
| 4,515,595 A | 5/1985 | Kievit et al. |
| 4,610,678 A | 9/1986 | Weisman et al. |
| 4,673,402 A | 6/1987 | Weisman et al. |
| 4,710,189 A | 12/1987 | Lash |
| 4,834,735 A | 5/1989 | Alemany et al. |
| 4,846,825 A | 7/1989 | Enloe et al. |
| 4,888,231 A | 12/1989 | Angstadt |
| 4,892,536 A | 1/1990 | Desmarais et al. |
| 4,940,464 A | 7/1990 | Van Gompel et al. |
| 4,990,147 A | 2/1991 | Freeland |
| 5,037,416 A | 8/1991 | Allen et al. |
| 5,092,861 A | 3/1992 | Nomura et al. |
| 5,137,537 A | 8/1992 | Herron et al. |

(Continued)

FOREIGN PATENT DOCUMENTS

GB    2 250 921 A    6/1992

(Continued)

OTHER PUBLICATIONS

International Search Report.

Primary Examiner — Michele M Kidwell
(74) Attorney, Agent, or Firm — William E. Gallagher

(57) ABSTRACT

A disposable absorbent article may comprise a chassis and a pair of longitudinally disposed barrier cuffs. Each cuff may contain a barrier zone, an attachment zone, and a transition edge separating the barrier zone and attachment zone. The barrier cuffs exhibit a cuff span and a cuff height at a given cross-section through a crotch point and an end region. The absorbent article exhibits a cuff span ratio, defined as a maximum cuff span as measured in the end region of the barrier cuff divided by a cuff span as measured at the crotch point, of greater than 1. The absorbent article exhibits a cuff height ratio, defined as a cuff height as measured at the crotch point divided by a minimum cuff height as measured in the end region, of greater than 1.

15 Claims, 10 Drawing Sheets

U.S. PATENT DOCUMENTS

| | | |
|---|---|---|
| 5,147,345 A | 9/1992 | Young et al. |
| 5,151,092 A | 9/1992 | Buell et al. |
| 5,221,274 A | 6/1993 | Buell et al. |
| 5,246,433 A | 9/1993 | Hasse et al. |
| 5,260,345 A | 11/1993 | Desmarais et al. |
| 5,269,775 A | 12/1993 | Freeland et al. |
| 5,342,338 A | 8/1994 | Roe |
| 5,387,207 A | 2/1995 | Dyer et al. |
| 5,397,316 A | 3/1995 | LaVon et al. |
| 5,527,302 A | 6/1996 | Endres et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,584,828 A | 12/1996 | Yamamoto et al. |
| 5,599,417 A | 2/1997 | Glaug et al. |
| 5,607,760 A | 3/1997 | Roe |
| 5,609,587 A | 3/1997 | Roe |
| 5,625,222 A | 4/1997 | Yoneda et al. |
| 5,635,191 A | 6/1997 | Roe et al. |
| 5,643,588 A | 7/1997 | Roe et al. |
| 5,667,609 A | 9/1997 | Liu |
| 5,735,838 A | 4/1998 | Ronnberg et al. |
| 5,769,838 A | 6/1998 | Buell et al. |
| 5,788,685 A | 8/1998 | Ronnberg et al. |
| 5,897,545 A | 4/1999 | Kline et al. |
| 5,957,908 A | 9/1999 | Kline et al. |
| 6,004,306 A | 12/1999 | Robles et al. |
| 6,013,589 A | 1/2000 | Desmarais et al. |
| 6,107,537 A | 8/2000 | Elder et al. |
| 6,120,487 A | 9/2000 | Ashton |
| 6,120,489 A | 9/2000 | Johnson et al. |
| 6,120,632 A | 9/2000 | Dragoo et al. |
| 6,183,459 B1 | 2/2001 | Yamamoto et al. |
| 6,508,798 B1 | 1/2003 | Widlund et al. |
| 6,881,205 B2 | 4/2005 | Zehner et al. |
| 7,482,505 B2 | 1/2009 | Stupperich et al. |
| 7,626,073 B2 | 12/2009 | Catalan |
| 2004/0162536 A1 | 8/2004 | Becker et al. |
| 2004/0167486 A1 | 8/2004 | Busam et al. |
| 2006/0282053 A1 * | 12/2006 | Rohrl .................. 604/385.01 |

FOREIGN PATENT DOCUMENTS

| | | |
|---|---|---|
| JP | 10-066710 A | 3/1998 |
| JP | 2001-008969 A | 1/2001 |
| WO | WO-94/10951 A1 | 5/1994 |
| WO | WO-95/13771 A1 | 5/1995 |
| WO | WO-95/31952 A1 | 11/1995 |
| WO | WO-97/41817 A1 | 11/1997 |
| WO | WO-98/19644 A1 | 5/1998 |
| WO | WO-2004/105668 A1 | 12/2004 |

* cited by examiner

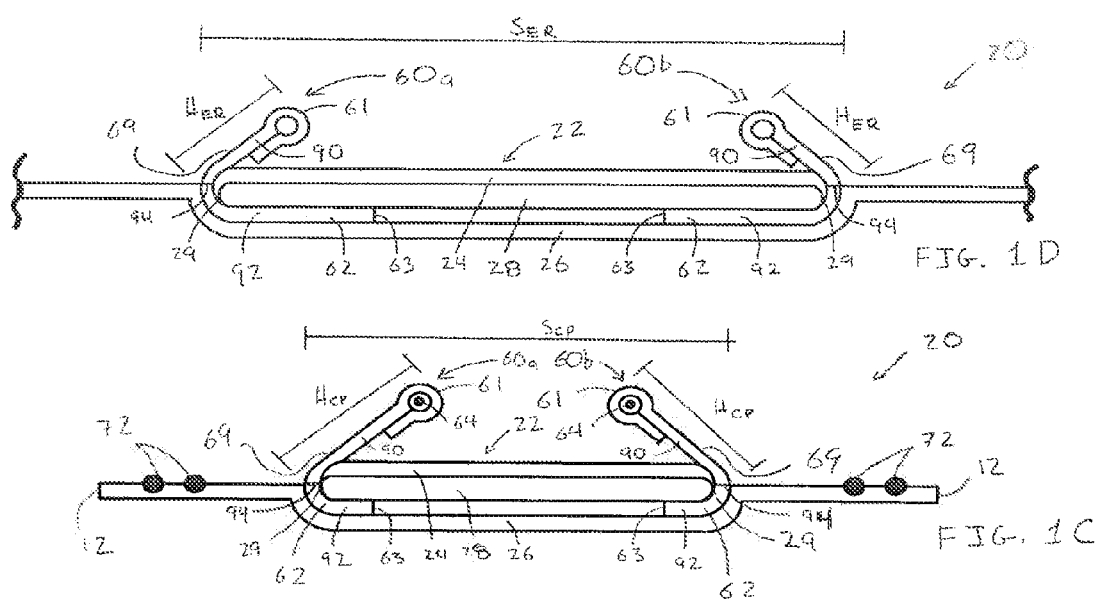

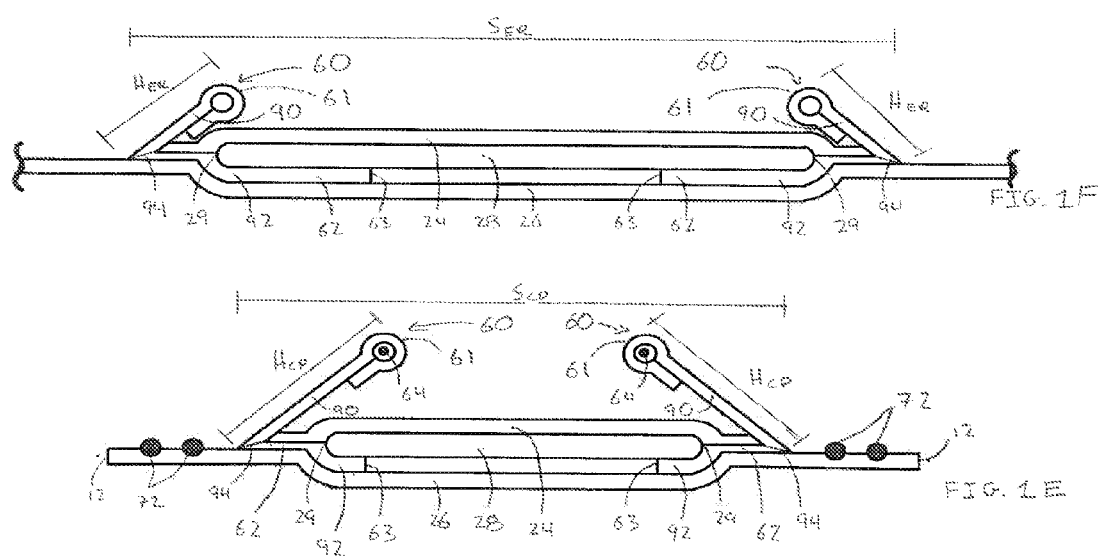

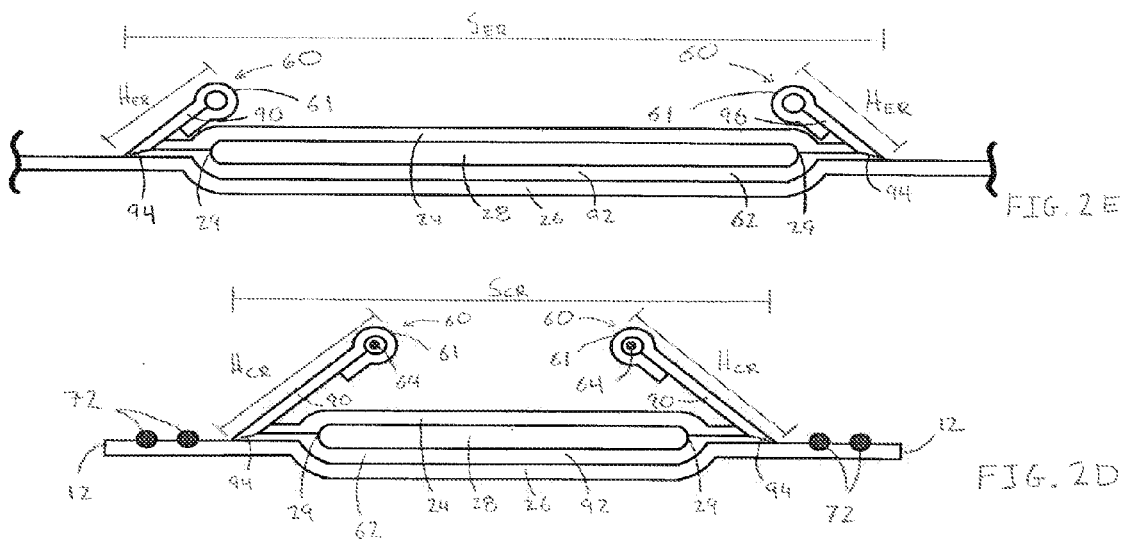

ABSORBENT ARTICLE HAVING A MULTI-DIMENSIONALLY CONTOURED BARRIER CUFF

CROSS REFERENCE TO RELATED APPLICATION

This application is a continuation of application Ser. No. 11/400,467, filed Apr. 7, 2006 now U.S. Pat. No. 7,666,175, the substance of which is incorporated herein by reference.

FIELD OF THE INVENTION

The present invention relates to absorbent articles, which are capable of absorbing bodily exudates, having contoured barrier kg cuffs. The contoured barrier leg cuffs are contoured with respect to the cuff height and the cuff span.

BACKGROUND OF THE INVENTION

The primary function of absorbent articles such as diapers, training pants, incontinence briefs, and the like is to absorb and contain body exudates. These articles are expected to prevent body exudates from escaping and soiling clothing, bedding, or other items that may come in contact with the article during wear. Absorbent articles have a variety of structures (e.g., superabsorbent polymers, leg cuffs, acquisition layers) designed to improve absorption and containment. Barrier cuffs are another structure common to absorbent articles.

Barrier cuffs (e.g., also referred to as inner cuffs, inner leg cuffs, leg gussets) are physical barriers which inhibit loose fecal material or gushes of urine or liquids from escaping the article. The barrier cuffs restrain the free flow of exudates and provide a structure to contain the exudates within the diaper. Typical barrier cuffs include a pair of flaps disposed longitudinally on the article running at least through the crotch region of the article. The barrier cuffs are laterally spaced so as to allow for the receipt of body exudates. Barrier cuffs typically comprise a spacing means associated with the barrier cuff that allows the barrier cuff to stand up and serve as a physical barrier to exudates leakage or runoff from the body-facing surface of the article. A common spacing means is an elastic member disposed along at least a portion of the upstanding edge of the barrier cuff. The elastic member not only allows the barrier cuff to stand-up but also allows the barrier cuff to conform to the shape of the wearer. However, barrier cuff construction can be improved.

Contemporary absorbent articles are continually modified to exhibit a more garment-like fit and appearance. Traditionally, absorbent articles like diapers have a rectilinear shape with a width in the crotch region ranging from about 180 mm to about 225 mm for a 22-37 lbs baby, but the perineal width of such a baby is approximately 38 mm. It is desirable to construct diapers having reduced width in the perineal area (i.e., crotch region). Diapers have made improvements such as exhibiting a more tapered, body-conforming shape. For example, diapers are constructed with absorbent cores having an hour-glass shape or a tapered midsection which further reduces width and bulk in the perineal area. However, other structures in the diaper continue to be less anatomically compliant. The barrier cuffs continue to be rectilinear in shape and configuration. The barrier cuffs are typically disposed longitudinally and are equally spaced in the diaper. Barrier cuffs having a rectilinear shape poorly conform to a wearer's anatomy. It is desirable that the barrier cuffs have a width in the perineal area that approximates the perineal width of the wearer. Generally, given a typical perineal width of 38 mm (for a 22-37 lbs. baby), the perineum is the narrowest point through which the barrier cuffs (or any other structure of the diaper) must travel.

Current barrier cuff construction may exacerbate sagging of the absorbent article in the front and/or back waist region. Upon being loaded with body exudates, the crotch region of the article is often drawn downward by the weight of the exudates. The downward loading force caused by the exudates is exacerbated by the elastic contraction force. The forces are coupled into the diaper chassis at points of attachment including points near the front and back waist regions. The communication of the loading force to opposing ends of the elastic members can result in disproportionate distribution of the force. This is due in part to the physical separation in the transverse dimension of the attachment points of the cuff to the chassis and the upstanding edge of the barrier cuff. In typical barrier cuff constructions, this separation distance also defines the height of the barrier cuff. As a result, localized areas extending from the ends of the elastic members and to the waist edge experience a higher relative amount of the loading force than regions adjacent to the localized areas. Functionally, these localized areas along the waist edge are prone to sag (i.e., the waist edge is drawn downward). Sagging can be minimized if the localized areas are spaced apart along the waist edge of the article. In other words, the terminal ends of the elastic members should be spaced as far apart as feasible so that the communicated loading force is less localized along the waist edge. The sagging can also be minimized by reducing the lateral distance between the attachment point of the cuff to the chassis and the upstanding edge of the barrier cuff as far away from the waist edge as possible so that the force of the elasticized member is more directly coupled into the diaper chassis further away from the waist region resulting in a delocalization of the elastic contraction force relative to the waist region. However, lateral distance is necessary in the crotch region for containment and barrier purposes.

A contradiction exists between the goals of providing barrier cuffs that have an anatomically conforming fit (i.e., narrow crotch) and that maximize the distribution of the loading force (i.e., wide waist). Furthermore, there is a contradiction between maximizing leakage protection by having a large upstanding portion of the barrier cuff within the narrow width of the crotch region. Added to the complexity of forming a barrier cuff that is narrow in the crotch and wide in the waist is the need for the barrier cuff to maintain optimal barrier properties. The barrier cuff should have a maximum height in the crotch region where body exudates are more likely to be contained. Conversely, the barrier cuff requires little to no height in the waist regions of the absorbent article. Within the waist regions, the barrier cuff may be compressed and prevented from standing upright. Cuff height in the waist regions is typically unnecessary for barrier purposes. Additionally, this unnecessary cuff height adds bulk to the waist region and may adversely impact wearer comfort.

Furthermore, the efficiency of material usage and cost concerns also play an important role in barrier cuff construction. Cuff height in the waist region is an unnecessary structure which results in added cost with little to no benefit to the absorbent article.

Therefore, in light of the problems presented above, it is desirable to provide an absorbent article having barrier cuffs that exhibit multidimensional contouring.

SUMMARY OF THE INVENTION

In one aspect, the present invention relates to an absorbent article having a body-facing surface, garment-facing surface, a front waist region, a rear waist region, and a crotch region between the front and rear waist regions. The absorbent article may comprise a chassis and a pair of longitudinally disposed barrier cuffs. The chassis may comprise a backsheet, a liquid permeable topsheet, and an absorbent core disposed between said backsheet and said topsheet. The pair of longitudinally disposed barrier cuffs each may comprise a barrier zone, an attachment zone, and a transition edge separating the barrier zone and attachment zone. The barrier cuff is joined to the chassis within the attachment zone. The barrier zone comprises a longitudinally extending elastic member joined to a barrier member such that the elastic member lifts said barrier zone away from the body-facing surface of absorbent article during wear of the absorbent article. The barrier cuffs exhibit a cuff span and a cuff height at a given cross-section through a crotch point and an end region. The absorbent article exhibits a cuff span ratio, defined as a maximum cuff span as measured in the end region of the barrier cuff divided by a cuff span as measured at the crotch point, of greater than 1. The absorbent article exhibits a cuff height ratio, defined as a cuff height as measured at the crotch point divided by a minimum cuff height as measured in the end region, of greater than 1.

In another aspect, the present invention relates to an absorbent article having a body-facing surface, garment-facing surface, a front waist region, a rear waist region, and a crotch region between the front and rear waist regions. The absorbent article may comprise a chassis and a pair of opposing longitudinally disposed barrier cuffs. The chassis may comprise a backsheet, a liquid permeable topsheet, and an absorbent core disposed between said backsheet and said topsheet. The pair of opposing longitudinally disposed barrier cuffs may comprise a barrier member having an upstanding longitudinal edge. The barrier member may be disposed at least partially between the absorbent core and the backsheet. The barrier member may extend laterally beyond the longitudinal edge of the absorbent core. The barrier cuff may comprise a longitudinally extending elastic member joined to the barrier member in proximity to the upstanding longitudinal edge such that the elastic member lifts a portion of the barrier member away from the body-facing surface of absorbent article during wear of the absorbent article. Each barrier cuff may comprise a barrier zone, an attachment zone, and a transition edge separating the barrier zone and attachment zone. The barrier cuffs exhibit a cuff span and a cuff height at a given cross-section through a crotch point and an end region. The topsheet may be disposed laterally between the opposing barrier cuffs. The absorbent article exhibits a cuff span ratio, defined as a maximum cuff span as measured in the end region of the barrier cuff divided by a cuff span as measured at the crotch point, of greater than 1. The absorbent article exhibits a cuff height ratio, defined as a cuff height as measured at the crotch point divided by a minimum cuff height as measured in the end region, of greater than 1.

In another aspect, the present invention relates to an absorbent article having a body-facing surface, garment-facing surface, a front waist region, a rear waist region, and a crotch region between the front and rear waist regions. The absorbent article may comprise a chassis and a pair of longitudinally disposed barrier cuffs. The chassis may comprise a backsheet, a liquid permeable topsheet, and an absorbent core disposed between said backsheet and said topsheet. The pair of longitudinally disposed barrier may comprise a barrier member having an upstanding longitudinal edge and a proximal longitudinal edge wherein the proximal longitudinal edge is joined to the topsheet. The pair of longitudinally disposed barrier cuffs comprise a longitudinally extending elastic member joined to the barrier member in proximity to the upstanding longitudinal edge such that said elastic member lifts a portion of the barrier member away from the topsheet during wear of the absorbent article. Each barrier cuff may have an attachment zone, which is a portion of the barrier cuff joined to the topsheet; a barrier zone, which is a portion of the barrier cuff that lifts away from the topsheet during wear of the absorbent article; and a transition edge separating the barrier zone and attachment zone. The barrier cuffs may exhibit a cuff span and a cuff height at a given cross-section through a crotch point and an end region. The absorbent article may exhibit a cuff span ratio, defined as a maximum cuff span as measured in the end region of the barrier cuff divided by a cuff span as measured at the crotch point, of greater than 1. The absorbent article may exhibit a cuff height ratio, defined as a cuff height as measured at the crotch point divided by a minimum cuff height as measured in the end region, of greater than 1.

BRIEF DESCRIPTION OF THE DRAWINGS

In the accompanying drawing, like reference numerals identify like elements, which may or may not be identical in the several exemplary embodiments that are depicted. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description.

FIGS. 1C-D are cross-sectional views of the diaper of FIG. 1A taken when the diaper is fastened and ready for wear.

FIGS. 1E-F are cross-sectional views of another embodiment of the diaper of FIG. 1A taken when the diaper is fastened and ready for wear.

FIGS. 2D-E are cross-sectional views of another embodiment of the diaper of FIG. 2A taken when the diaper is fastened and ready for wear.

DETAILED DESCRIPTION OF THE INVENTION

Figure 1A:
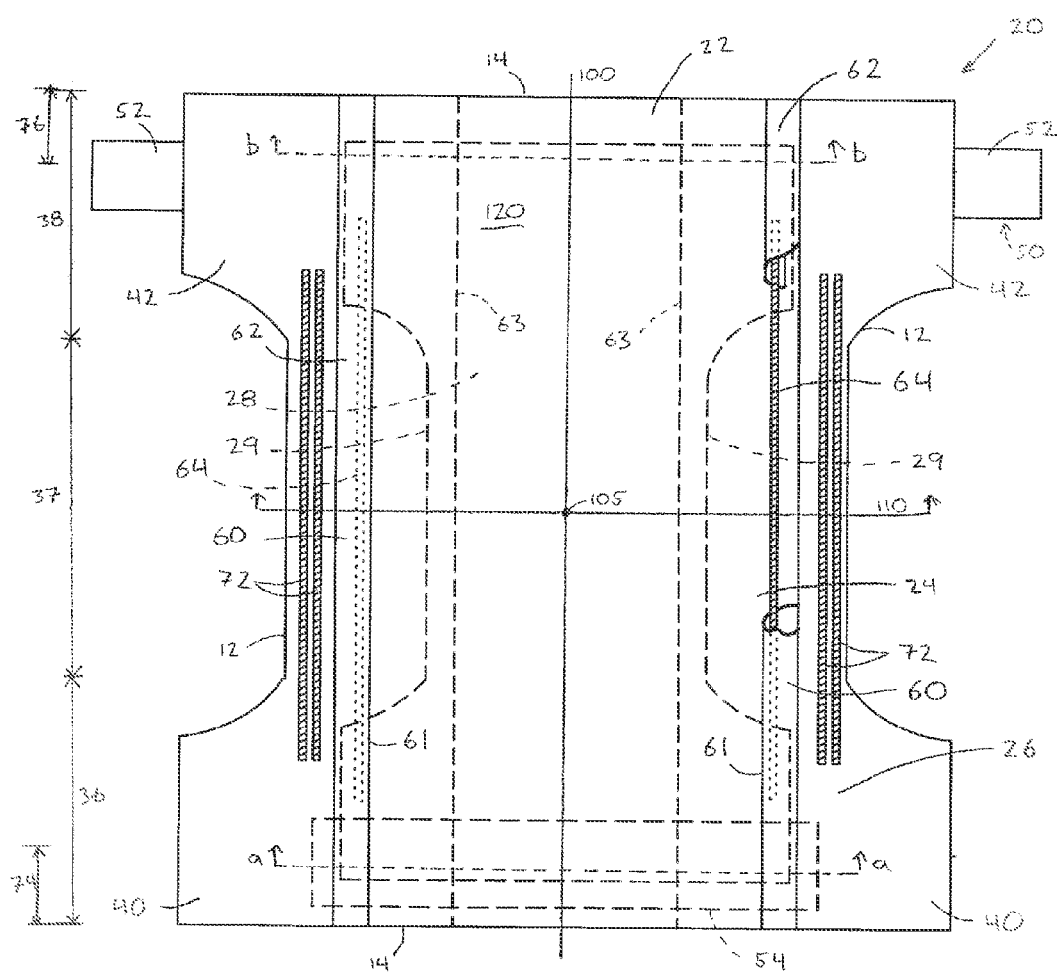
FIG. 1A is a plan view of an exemplary, non-limiting embodiment of an absorbent article in the form of a diaper having contoured barrier cuffs.

As used herein, the following terms shall have the meaning specified thereafter:

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like. Absorbent articles may be disposable or may have portions that may be restored or renewed.

"Proximal" and "Distal" refer respectively to the location of an element relatively near to or far from the longitudinal or lateral centerline of a structure.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal"

"Lateral" refers to a direction running from a longitudinal edge to an opposing longitudinal edge of the article and generally at a right angle to the longitudinal direction. Directions within 45 degrees of the lateral direction are considered to be "lateral."

"Longitudinal Centerline" refers to a longitudinal line that can be drawn through the middle of an absorbent article. For most absorbent articles, the longitudinal centerline separates the article into two substantially symmetrical halves that will fall on the left and right halves of a wearer during wear.

"Lateral Centerline" refers to a lateral line drawn through the midpoint of the longitudinal centerline and perpendicular to the longitudinal centerline.

"Crotch Point" refers to a point of intersection between the longitudinal centerline and the lateral centerline.

"End Region(s)," when used in reference to a contoured barrier cuff, refers to one or more portions of the contoured barrier cuff wherein all points within the portion are no more than 2.5 cm from the closest lateral edge of the barrier cuff. For most absorbent articles, each contoured barrier cuff will have a two opposing end regions, a front end region disposed in the front waist region of the absorbent article and a rear end region disposed in the rear waist region of the absorbent article.

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Extendibility" and "extensible" mean that the width or length of the component in a relaxed state can be extended or increased.

"Elastic," "elastomer," and "elastomeric" refer to a material which generally is able to extend to a strain of at least 50% without breaking or rupturing, and is able to recover substantially to its original dimensions after the deforming force has been removed.

"Elastomeric material" is a material exhibiting elastic properties. Elastomeric materials may include elastomeric films, scrims, nonwovens, and other sheet-like structures.

"Outboard" and "inboard" refer respectively to the location of an element disposed relatively far from or near to the longitudinal centerline of the diaper with respect to a second element. For example, if element A is outboard of element B, then element A is farther from the longitudinal centerline than is element B.

"Pant" or "Pants" refers to an absorbent article having a pre-formed waist and leg openings. A pant may be donned by inserting a wearer's legs into the leg openings and sliding the pant into position about the wearer's lower torso. Pants are also commonly referred to as "closed diapers," "prefastened diapers," "pull-on diapers," "training pants," and "diaper-pants."

"Laminated structure" or "laminate" means a structure in which one layer, material, component, web, or substrate is adhesively bonded, at least in part, to another layer, material, component, web, or substrate.

"Attachment zone" refers to a portion of a barrier cuff that is directly joined to the chassis of the absorbent article or that is otherwise prevented from lifting lift away from the body-facing surface of the absorbent article during wear. Portions of the barrier cuff disposed between the absorbent core and the backsheet are considered to be in the attachment zone.

"Barrier Zone" refers to a portion of a barrier cuff that lifts away from the body-facing surface of the absorbent article during wear of the absorbent article.

"Transition Edge" refers to the boundary between the barrier zone and the attachment zone on a barrier cuff.

"Contoured Barrier Cuffs" refer to barrier cuffs that are contoured with respect to cuff height and cuff span.

FIG. 1A is a plan view of an exemplary, non-limiting embodiment of an absorbent article of the present invention in the form of a diaper 20. The diaper 20 is shown in a flat, uncontracted state (i.e., without elastic induced contraction). The body-facing surface 120 of the diaper 20 is facing the viewer and the garment-facing surface is away from the viewer. The diaper 20 includes a longitudinal centerline 100 and a lateral centerline 110 which intersect to form a crotch point 105. The diaper 20 may comprise a chassis 22. The diaper 20 and chassis 22 are shown to have a front waist region 36, a rear waist region 38 opposed to the front waist region 36, and a crotch region 37 located between the front waist region 36 and the rear waist region 38. The outer periphery of chassis 22 is defined by longitudinal side edges 12 and lateral end edges 14 (which may be referred to as the waist edge). The chassis 22 may have opposing longitudinal side edges 12 that are oriented generally parallel to the longitudinal centerline 100. However, for better fit, longitudinal side edges 12 may be curved or angled to produce, for example, an "hourglass" shape diaper when viewed in a plan view. The chassis 22 may have opposing end edges 14 that are oriented generally parallel to the lateral centerline 110; however the end edges 14 may be curved or angled to provide a more contoured diaper 20.

The chassis 22 is the main body of the diaper 20. Other structures may be added to the chassis 22 to improve the fit and/or functionality of the resulting diaper 20. The chassis 22 comprises at least a liquid permeable topsheet 24, a backsheet 26, and an absorbent core 28 between the topsheet 24 and the backsheet 26. The topsheet 24 may be joined to the core 28 and/or the backsheet 26. The backsheet 26 may be joined to the core 28 and/or the topsheet 24. It should be recognized that other structures, elements, or substrates may be positioned between and the topsheet 24, core 28, and/or backsheet 26. While the topsheet 24, the backsheet 26, and the absorbent core 28 may be assembled in a variety of well-known configurations, preferred diaper configurations are described generally in U.S. Pat. Nos. 3,860,003; 5,151,092; 5,221,274; 5,554,145; 5,569,234; 5,580,411; and 6,004,306.

The topsheet 24 is generally a portion of the diaper 20 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. In certain embodiments, at least a portion of the topsheet 24 is liquid pervious, permitting liquid to readily penetrate through the thickness of the topsheet 24. A particularly preferred topsheet 24 is available from BBA Fiberweb, Brentwood, Tenn. as supplier code 055SLPV09U.

Any portion of the topsheet 24 may be coated with a lotion (as described in U.S. Pat. Nos. 5,607,760; 5,609,587; 5,635,191; and 5,643,588) and/or may be fully or partially elasticized or may be foreshortened so as to provide a void space between the topsheet 24 and the core 28 (as described in more detail in U.S. Pat. Nos. 4,892,536; 4,990,147; 5,037,416; and 5,269,775).

The core 28 has opposing longitudinal edges 29 that are oriented generally parallel to the longitudinal centerline 100. However, the core longitudinal edges 29 may be curved or angled to produce, for example as shown in the FIG. 1A, an "hourglass" shape when viewed in a plan view. The absorbent core 28 may comprise a wide variety of liquid-absorbent materials commonly used in disposable diapers and other absorbent articles. Examples of suitable absorbent materials include comminuted wood pulp (e.g., air felt creped cellulose wadding); melt blown polymers including co-form; chemically stiffened, modified or cross-linked cellulosic fibers; wraps and tissue laminates; absorbent foams; absorbent sponges; superabsorbent polymers; absorbent gelling materials; or any other known absorbent material or combinations of materials. The absorbent core 28 may comprise a fluid acquisition component which acquires fluid exudates and partitions the exudates away from a wearer's body, a fluid distribution component which distributes/redistributes fluid exudates points away from the point of initial exudate loading, and/or a fluid storage component which retains a majority of the fluid exudates on a weight basis. A suitable absorbent core 28 comprising an acquisition layer, a distribution layer, and/or a storage layer is described in U.S. Pat. No. 6,013,589.

Another suitable absorbent core construction is described in U.S. Publication No. 2004/0167486 to Busam et al. The absorbent core of the aforementioned publication uses no or minimal amounts of absorbent fibrous material within the core. Generally, the absorbent core may include no more than about 20% weight percent of absorbent fibrous material (i.e., [weight of fibrous material/total weight of the absorbent core]×100).

In certain embodiments, the absorbent core 28 may also include layers to stabilize the core components. Such layers include a core cover and a core forming layer. A suitable material for such layers is a spunbonded/meltblown/spunbonded nonwoven having a basis weight between about 10 and 15 g/m² (the meltblown layer comprises <5 g/m²) available from Avgol America, Inc. of Knoxville, N.C. Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316; and 5,625,222 and in U.S. Publication Nos. 2004/0162536.

In certain embodiments, the absorbent core 28 may comprise a core wrap. The core wrap at least partially covers the liquid absorbent material of the absorbent core 28. Typically, the core wrap is disposed on a body-facing surface of the absorbent core 28. The core wrap may be useful in immobilizing the liquid absorbent material of the absorbent core 28. The core wrap may comprise a liquid pervious substrate such as a tissue or nonwoven web.

The diaper 20 may comprise other optional structures such as a forming layer adjacent to and, typically, underlying the absorbent core 28. The forming layer is typically disposed between the absorbent core 28 and the backsheet 26. The forming layer provides a substrate on which to deposit the liquid absorbent material during manufacture of the absorbent core 28. In certain embodiments, the forming layer is an air permeable nonwoven web such as described in U.S. Pat. No. 4,888,231.

The backsheet 26 is generally positioned such that it may comprise a portion of the garment-facing surface of the diaper 20. The backsheet 26 may be designed to prevent the exudates absorbed by and contained within the diaper 20 from soiling articles that may contact the diaper 20, such as bed sheets and undergarments. In certain embodiments, the backsheet 26 is substantially urine-impermeable (e.g., liquid water cannot pass through the thickness of the backsheet in the absence of a forcing pressure). Suitable backsheet 26 materials include films such as those manufactured by Tredegar Industries Inc. of Terre Haute, Ind. and sold under the trade names X15306, X10962, and X10964. Other suitable backsheet 26 materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

In certain embodiments, the backsheet 26 may also consist of more than one layer. For example, the backsheet 26 may comprise an outer cover and an inner layer or may comprise two outer covers with an inner layer disposed therebetween. The outer cover may comprise a material having a soft, cloth-like feel such as a soft, non-woven material. The inner layer may comprise a material having suitable barrier characteristics to prevent leakage from the diaper 20. The inner layer may comprise a substantially water-impermeable film or any other suitable backsheet material as presented above. The outer cover and an inner layer may be joined together by adhesive or any other suitable material or bonding technique.

A suitable outer cover is available from Corovin GmbH, Peine, Germany as supplier code A18AH0 and a suitable inner layer is available from RKW Gronau GmbH, Gronau, Germany as supplier code PGBR4WPR.

The diaper 20 may include other structures. The diaper 20 may include a fastening system 50. When fastened, the fastening system 50 interconnects the front waist region 36 and the rear waist region 38. When fastened, the diaper 20 contains a circumscribing waist opening and two circumscribing leg openings. The fastening system 50 may comprise an engaging member 52 and a receiving member 54. The engaging member 52 may comprise hooks, loops, an adhesive, a cohesive, a tab, or other fastening mechanism. The receiving member 54 may comprise hooks, loops, a slot, an adhesive, a cohesive, or other fastening mechanism that can receive the engaging member 52. Suitable engaging member 52 and receiving member 54 combinations are well known in the art and include but are not limited to hooks/loop, hooks/hooks, adhesive/polymeric film, cohesive/cohesive, adhesive/adhesive, tab/slot, and button/button hole.

The diaper 20 may comprise one or more leg elastic members 72. The leg elastic members 72 are generally disposed adjacent the longitudinal side edges 12 of the diaper 20. The leg elastic members 72 tend to gather and hold the diaper 20 against the legs of the wearer. The leg elastic members 72 may serve a gasketing function preventing body exudates from leaking out of the diaper 20. The leg elastic members 72 may be joined to or between any of the substrates within the diaper 20 such as the topsheet 24 or backsheet 26. The portion of the diaper gathered by the leg elastic member 72 may be known as an outer leg cuff, a leg gasket, or an elastic cuff. Suitable gasketing cuff construction is further described in U.S. Pat. No. 3,860,003.

The diaper 20 may further comprise waist elastic members (not shown) that are generally disposed adjacent the lateral end edges 14 of the diaper 20 in the front waist region 36 and/or the rear waist region 38. Waist elastic members generally will allow for lateral elongation and recovery. Waist elastic members may be joined to or between any of the substrates within the diaper 20 such as the topsheet 24 or backsheet 26. The waist elastic member may improve the fit and containment of the diaper 20. Other suitable configurations of the elastic waist feature are described in U.S. Pat. Nos. 4,515,595; 4,710,189; 5,151,092; and 5,221,274.

The diaper 20 may include front ears 40 and back ears 42. In certain embodiments, the front and/or back ears 40, 42 may be unitary elements of the diaper 20 (i.e., the ears are not separately manipulative elements secured to the diaper 20, but rather are formed from and are extensions of one or more of the various layers of the chassis 22; such ears are may be referred to as "side-notch ears"). The diaper 20 for FIG. 1A includes unitary front and back ears 40, 42. In certain embodiments, the front and/or back ears may be discrete elements that are joined to the chassis 22. Discrete front and/or back ears may be joined to the chassis 22 by any bonding method known in the art. Discrete ears may comprise a layer, element, or substrate that extends from the chassis 22. The front and back ears may be extensible, inextensible, elastic, or inelastic. The front and back ears may be formed from any nonwoven webs, woven webs, knitted fabrics, polymeric and elastomeric films, apertured films, sponges, foams, scrims, and combinations and laminates thereof. In certain embodiments the front and back ears may be formed of a nonwoven/elastomeric material laminate or a nonwoven/elastomeric material/nonwoven laminate. A suitable elastic ear may be formed form a laminate comprising an elastomeric film (such as supplier code X25007 from Tredegar Corp, Richmond, Va.) disposed between two nonwoven layers (such as supplier code FPN332 from BBA Fiberweb, Brentwood, Tenn.).

In alternative embodiments, the diaper 20 may be preformed by the manufacturer to create a pant. A pant may be preformed by any suitable technique including, but not limited to, joining together portions of the article using refastenable and/or non-refastenable bonds (e.g., seam, weld, adhesive, cohesive bond, fastener, etc.) in certain embodiments, the diaper 20 may be manufactured with the fastening system 50 engaged (i.e., the engaging member 52 is joined to the receiving member 54). Suitable pants are disclosed in U.S. Pat. Nos. 5,246,433; 5,569,234; 6,120,487; 6,120,489; 4,940,464; 5,092,861; 5,897,545; and 5,957,908.

Figure 1B:
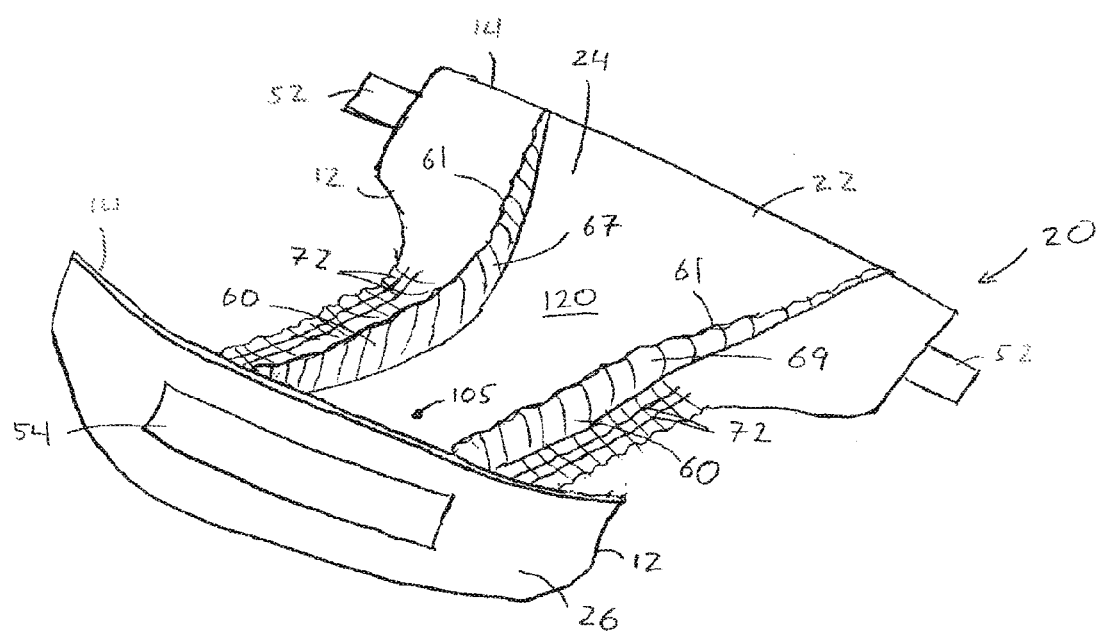
FIG. 1B is a perspective view of the diaper of FIG. 1A in a partially contracted state illustrating the contoured barrier cuffs lifting away from the body-facing surface of the diaper.

The diaper 20 comprises a pair of contoured barrier cuffs (collectively referenced as item 60) each having at least an upstanding longitudinal edge 61. In certain embodiments, such as shown in FIG. 1A, the contoured barrier cuffs 60 each have a proximal longitudinal edge 63. The contoured barrier cuffs 60 extend into the front waist region 36 and the rear waist region 38 and may comprise a front end region 74 and a rear end region 76. The contoured barrier cuffs 60 typically span the crotch region 37. The contoured barrier cuffs 60 comprise a barrier member 62 and a spacing mechanism associated with the barrier member 62. In certain embodiments, such as shown in FIG. 1A, the spacing mechanism may be a spacing elastic member 64 joined to the barrier member 62. The spacing elastic member 64 may be disposed proximate to the upstanding edge 61 of the contoured barrier cuff 60. The spacing elastic member 64 may be joined to the barrier member 62 continuously or discontinuously along the length of the spacing elastic member 64. The spacing elastic member 64 may be joined to the barrier member 62 at opposing longitudinal ends of the spacing elastic member 64. During wear, the spacing mechanism allows a portion of the contoured barrier cuff 60 (including a portion of the upstanding edge 61) to lift away from the body-facing surface 120 of the diaper 20 and toward the skin of a wearer. FIG. 1B is a perspective view of the diaper 20 of FIG. 1A in a partially contracted state that illustrates the contoured barrier cuffs 60 lifting away from the body-facing surface 120 of the diaper 20. The contoured barrier cuffs 60 further comprise an inboard surface 67 and an outboard surface 69. Contoured barrier cuffs 60 may also be referred to as second cuffs, inner leg cuffs or "stand-up" elasticized flaps.

The barrier member 62 may comprise a variety of substrates such as plastic films and woven or nonwoven webs of natural fibers, synthetic, or a combination of natural and synthetic fibers. In certain embodiments, the barrier member 62 may comprise a nonwoven web such as spunbond webs, meltblown webs, carded webs, and combinations and/or laminates thereof (e.g., spunbond-meltblown composites and variants). It may be desirable for the barrier member 62 to be substantially rectilinear (e.g., bounded by straight lines that may or may not meet at substantially right angles). In certain embodiments, the barrier member 62 is rectangular in shape. Rectilinear barrier members 62 may reduce the processing complexity compared to barrier members 62 having curvilinear edges.

Figure 2A:
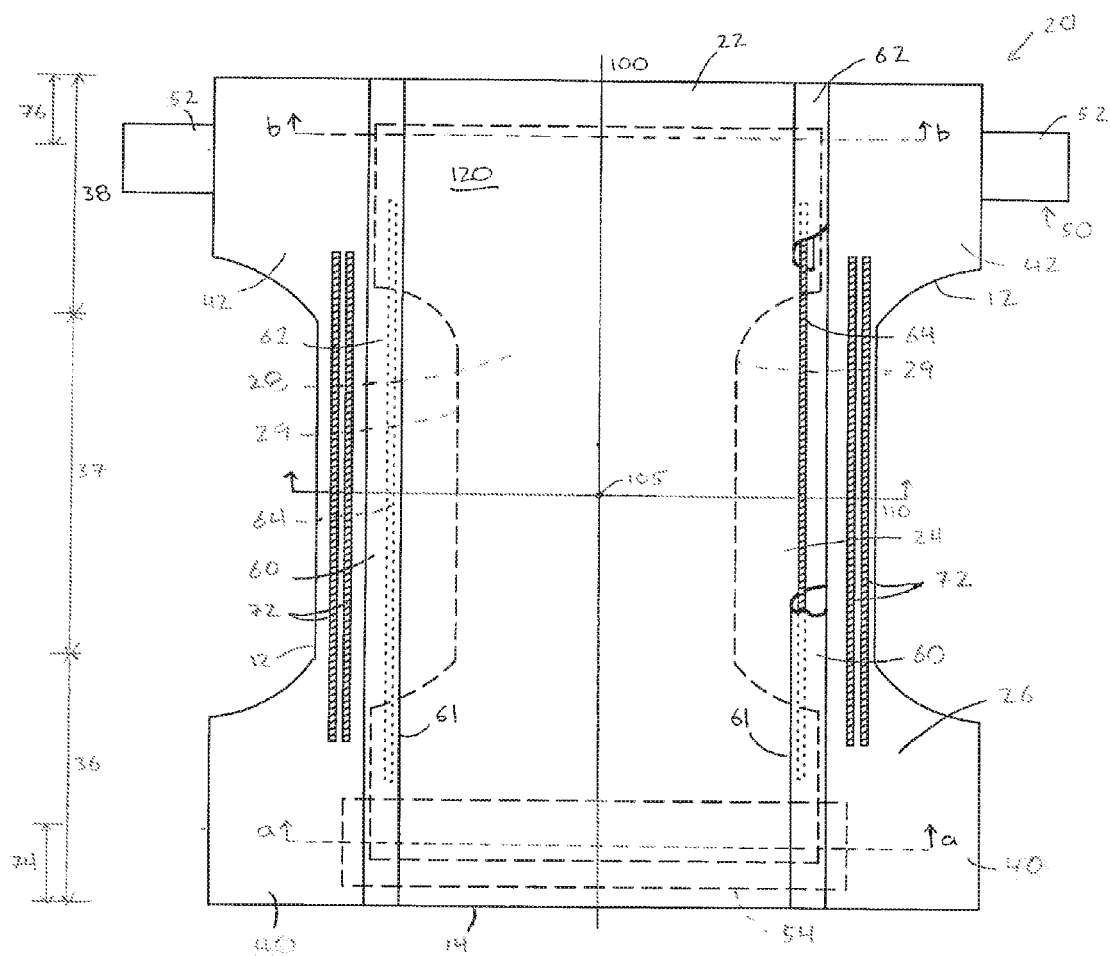
FIG. 2A is a plan view of a plan view of another embodiment of diaper having contoured barrier cuffs.

A suitable contoured barrier cuff 60 may have a nonwoven barrier member 62 available from BBA Fiberweb, Brentwood, Tenn. (supplier code 30926) and a spacing elastic member 64 available from Invista, Wichita, Kans. (supplier code T262P). The barrier member 62 may be fully or partially coated with a hydrophobic surface coating as detailed in U.S. Publication No. 2005/0177123. The elastic member 64 generally may span the longitudinal length of the contoured barrier cuff 60. In other embodiments, the elastic member 64 may span at least the longitudinal length of the barrier cuff 60 within the crotch region 37. The elastic member 64 may be continuously or discontinuously bonded to the barrier member 62. In certain embodiments, the elastic member 64 is bonded along portions of the opposing longitudinal ends with a substantial portion between either end being unbonded. It is desirable that the elastic member 64 exhibits sufficient elasticity such that a portion of the upstanding edge 61 of the contoured barrier cuff 60 remains in contact with the wearer during normal wear, thereby enhancing the barrier properties of the contoured barrier cuff 60. In certain embodiments, the elastic member 64 is disposed proximate to the upstanding edge 61. However, in other embodiments, the elastic member 64 may be disposed at a point between the upstanding edge 61 and the proximal edge 63 (or between opposing upstanding edges 61 in embodiments where the barrier cuffs 60 comprise a continuous barrier member 62 such as shown in FIG. 2A). In certain embodiments, the barrier material 62 may be folded over onto itself and, optionally, may be bonded to itself so as to encircle the elastic member 64. The barrier cuff 60 may comprise multiple elastic members 64. When multiple elastic member 64 are present, the elastic members 64 may be disposed proximate to each other or may be disposed in a spaced relation (e.g., one elastic member disposed along the upstanding edge 61 and one member disposed at a point between the upstanding edge 61 and the proximal edge 63).

During wear, the contoured barrier cuff 60 comprises at least two zones, a barrier zone 90 and an attachment zone 92. The barrier zone 90 and the attachment zone 92 may be seen in the cross-sectional views of FIGS. 1C-D. FIG. 1C is a cross-section of the diaper 20 of FIG. 1A taken along the lateral centerline 110. FIG. 1D illustrates a cross-section view of the diaper 20 of FIG. 1A taken along sectional line a-a in the front end region 74 or section line b-b in the rear end region 76. The attachment zone 92 is the portion of the barrier cuff 60 that is directly joined to the chassis 22 (i.e., specifically in this embodiment, the barrier cuff 60 is joined to the backsheet 26) or is otherwise prevented from lifting lift away from the body-facing surface 120 of the diaper 20 during wear. The attachment zone 92 may be joined to the chassis 22 by one or more bonds. Any suitable bonding method well known in the art may be used such as adhesive bonding, pressure bonding, heat bonding, autogenous bonding, ultrasonic bonding, and the like. The entire attachment zone 92 may be directly joined to the chassis 22 or discrete portions of the attachment zone 92 may be joined to the chassis 22. The portions of the attachment zone 92 that are not directly joined to the chassis 22 may be prevented from lifting away from the body-facing surface 120 of the diaper 20 during wear, for example, by being in proximity to a directly bonded portion of the attachment zone 92, being disposed between two or more directly bonded portions of the attachment zone 92, or being disposed underneath (i.e., body-facing surface of the attachment zone 92 is covered by) another substrate or structure that prohibits the attachment zone 92 lifting lift away from the body-facing surface 120.

The barrier zone 90 is the portion of the barrier cuff 60, which includes a portion of the upstanding edge 61 that may lift away from the body-facing surface 120 of the diaper 20. The barrier zone 90 forms a physical barrier preventing body exudates from flowing laterally out of the diaper 20. In some embodiments, the barrier zone 90 may be inflected inward toward the longitudinal centerline 100 along a portion of the longitudinal length of the barrier cuff 60; however, in other embodiments, the barrier zone 90 may extend substantially perpendicular to the body-facing surface 120 of the diaper 20 or may be deflected outward from the longitudinal centerline 100. The barrier zone 90 and the attachment zone 92 may meet at a transition edge 94. In a plan view of the diaper 20, the transition edge 94 may be connected to form a continuous (i.e., unbroken) line, series of line segments, or curve.

The contoured barrier cuffs 60 may be contoured in at least two aspects: cuff height H and cuff span S. The cuff height H is the lateral width of the barrier zone 90 of the contoured barrier cuff 60 at a given lateral cross-section. The cuff height H is measured by placing a rigid ruler, parallel to the lateral centerline 110, on the outboard surface 69 of the contoured barrier cuff 60. If the contoured barrier cuff 60 is gathered, crimped, or otherwise shortened in the lateral direction (such as by a spacing elastic member 64), the contoured barrier cuff 60 is to be elongated such that the fully extended width of the contoured barrier cuff 60 is considered. To make the measurement, it may be necessary to affix (e.g., tape or pin) the barrier cuff 60 in an elongated configuration to another rigid surface. The cuff height H is measured from the upstanding edge 61 to the transition edge 94. The cuff height H at a particular lateral cross-section evidences the amount of contoured barrier cuff 60 available for the barrier zone 90. The contoured barrier cuffs 60 exhibit a crotch point cuff height $H_{CP}$ which is the cuff height as measured at the crotch point 105 of the diaper 20, as shown in FIG. 1C. As shown in FIG. 1D, the contoured barrier cuffs 60 exhibit an end region cuff height $H_{ER}$ which is the minimum cuff height measured in either end region 74, 76. In some instances, it may be necessary to specify the cuff height in a specific end region. In such instances, the front end region cuff height is designated $H_{FER}$ and the rear end region cuff height is designated $H_{RER}$.

The diaper 20 of the present invention possesses a cuff height ratio, which is calculated by taking the crotch point cuff height $H_{CP}$ and dividing by the end region cuff height $H_{ER}$. In certain embodiments, the cuff height ratio is greater than 1. In other embodiments, the cuff height ratio may be greater than 1.5, 2, 3, 4, or, alternately, 5. Upon review of specific embodiments, as will be described below, one will recognize that the cuff height ratio may exceed 10 or more. An increased cuff height ratio evidences a more dramatic contouring in the height of the barrier cuff. The contouring of height solves the contradiction of providing a barrier cuff that exhibits maximum barrier and containment function in the crotch region while minimizing bulk and material in the waist regions.

In specific embodiments, the diaper 20 may be described as having a front cuff height ratio and/or a rear cuff height ratio, which are calculated by taking the crotch point cuff height $H_{CP}$ and dividing by the front end region cuff height $H_{FER}$ or the rear end region cuff height $H_{RER}$, respectively. In certain embodiments, the front cuff height ratio and/or the rear cuff height ratio is greater than 1. In other embodiments, the front cuff height ratio and/or the rear cuff height ratio may be greater than 1.5, 2, 3, 4, or, alternately, 5. Upon review of specific embodiments, as will be described below, one will recognize that the front cuff height ratio and or the rear cuff height ratio may exceed 10 or more.

The contoured barrier cuffs 60 may be contoured in span. The cuff span S is the lateral width between the transition edges 94 of opposing contoured barrier cuffs 60. The cuff span S is measured by placing a rigid ruler parallel to the lateral centerline and on the body-facing surface 120 of the diaper 20. Measurements are performed against a flat, unyielding surface such as a table top. The measurement is taken with the diaper 20 in a flat, uncontracted state (i.e., without elastic induced contraction). Pressure may be applied to the ruler while performing the measurement, if needed, to compress the core 28, which may have some degree of caliper preventing the ruler from laying flat against the underlying substrates (e.g., backsheet 26) of the diaper 20. The cuff span S is measured from the transition edge 94 of one contoured barrier cuff 60 to the transition edge 94 of the opposing barrier cuff 60. As shown in FIG. 1C, the contoured barrier cuffs 60 exhibit a crotch point span $S_{CP}$ which is the cuff span as measured at the crotch point 105 of the diaper 20. As shown in FIG. 1D, the contoured barrier cuffs 60 exhibit an end region span $S_{ER}$ which is the maximum cuff span measured in either end region 74, 76. In some instances, it may be necessary to specify the cuff span in a specific end region. In such instances, the front end region span is designated $S_{FER}$ and the rear end region span is designated $S_{RER}$.

The diaper 20 of the present invention possesses a cuff span ratio, which is calculated by taking the end region span $S_{ER}$ and dividing by the crotch point span $S_{CP}$. In certain embodiments, the cuff span ratio is greater than 1. In other embodiments, the cuff span ratio may be greater than 1.25, 1.5, 1.75, or, alternately, 2. An increased cuff span ratio evidences a more dramatic contouring of the span between the barrier cuffs. The contouring of span solves the contradiction of providing barrier cuffs that are wide in some regions and narrow in other regions. The present cuffs are well spaced in the waist end regions so as to more evenly distribute load thereby reducing sagging. Additionally, the present cuffs are narrow in the crotch region which provides a more anatomically compliant shape.

In specific embodiments, the diaper 20 may be described as having a front cuff span ratio and/or a rear cuff span ratio, which are calculated by taking the front end region span. $S_{FER}$ or the rear end region span $S_{RER}$, respectively, and dividing by the crotch point span $S_{CP}$. In certain embodiments, the front cuff span ratio and/or the rear cuff span ratio is greater than 1. In other embodiments, the front cuff height ratio and/or the rear cuff height ratio may be greater than 1.25, 1.5, 1.75, or, alternately, 2.

In certain embodiments of the present invention including the following illustrated embodiments, the diaper 20 comprises contoured barrier cuffs 60 that are contoured in respect to both cuff height H and cuff span S. Specifically, in certain embodiments, the contoured barrier cuffs 60 may exhibit a cuff height ratio of greater than 1 and a cuff span ratio of greater than 1. Alternately, the contoured barrier cuffs 60 may exhibit any combination of cuff height ratio being greater than 1, 1.5, 2, 3, 4, or 5 and cuff span ratio being greater than 1, 1.25, 1.5, 1.75, or 2. Furthermore, the present invention covers any combination of previously recited cuff height ratio, front cuff height ratio, rear cuff height ratio, cuff span ratio, front span ratio, and rear span ratio.

One suitable embodiment of a diaper having contoured barrier cuffs is shown in the cross-sectional views of FIG. 1C-D are cross-sectional views of the diaper 20 of FIG. 1A taken when the diaper is fastened (e.g., fastening system, if present, is engaged) and ready for wear (e.g., diaper forms two leg openings and a waist opening). In this embodiment, the contoured barrier cuffs 60 are shown as being partially disposed between the absorbent core 28 and the backsheet 26. Each barrier cuff 60 comprises a discrete barrier member 62 and a spacing elastic member 64 (present in FIG. 1C). The second longitudinal edge 63 of the contoured barrier cuff 60 may be disposed inboard of the longitudinal edge 29 of the core 28. The attachment zone 92 of the barrier cuff 60 is generally the portion of the barrier member 62 disposed between the absorbent core 28 and the backsheet 26. The attachment zone 92 may be joined to the backsheet 26, the absorbent core 28, or both.

The barrier cuff 60 is shown extending away from the body-facing surface of the diaper 20 to form the barrier zone 90. The barrier zone 90 includes the upstanding edge 61 and the spacing elastic member 64. In this embodiment (as well as the other embodiments illustrated herein), the barrier member 62 is shown to encircle the spacing elastic member 64. However, the elastic member 64 may be disposed on or within the barrier member 62 without the need for encircling by the barrier member 62. The transition edge 94 is shown separating the barrier zone 90 from the attachment zone 92. It should be appreciated that the transition edge 94 is the boundary between the barrier zone 90 and attachment zone 92. Although the transition edge 94 is shown as being a line through the barrier cuff 60, the line is symbolic and does not suggest the existence of a physical line in the diaper 20.

FIG. 1C is a cross-section taken through the crotch point of the diaper (i.e., the sectional line in FIG. 1A is the lateral centerline). FIG. 1C shows the crotch point cuff height $H_{CP}$ and the crotch point span $S_{CP}$. FIG. 1D shows the end region cuff height $H_{ER}$ and the end region span $S_{ER}$. FIG. 1D is representative of a cross-section taken through either sectional line a-a in the front end region of the diaper in FIG. 1A or sectional line b-b in the rear end region of the diaper in FIG. 1A. While FIGS. 1A-D are not to be taken as drawn to scale, one should appreciate that the crotch point cuff height $H_{CP}$ is greater than the end region cuff height $H_{ER}$. Furthermore, one should appreciate that the crotch point span $S_{CP}$ is less than end region span $S_{ER}$. Having the barrier cuff 60 disposed under the core 28 and wrapping about the longitudinal edges 29 of the core, the available barrier zone 90 changes to a degree that is approximately proportional to the width of the core 28. Specifically for this embodiment, the wider portions of the core 28 translate into cuffs having reduced height and wider span. Conversely, the narrower regions of the core 28 translate into cuffs having increased height and narrower span.

For this embodiment, the crotch point cuff height $H_{CP}$ may be 37 mm and the crotch point span $S_{CP}$ may be 70 mm. The end region cuff height $H_{ER}$ may be 17 mm and the end region span $S_{ER}$ may be 110 mm. However, specific dimensions may vary particularly when diapers 20 are produced on high speed machinery. The cuff height ratio is greater than 1. However, the cuff height ratio may be greater than 1.5, 2, 3, 4, 5, or 10. The cuff span ratio is greater than 1. However, the cuff span ratio may be greater than 1.25, 1.5, 1.75, or 2.

In this embodiment, the topsheet 24 is disposed between the contoured barrier cuffs 60. The topsheet 24 is shown having a lateral width that is about equal to the lateral width of the absorbent core 28. In other embodiments, portions of the topsheet 24 may extend laterally outboard of the longitudinal edges 29 of the core 28 and may be joined to the contoured barrier cuff 60. The topsheet 24 may be joined to the barrier zone 90 of the barrier cuff 60, which may provide enhanced barrier protection. The topsheet 24 may be disposed along the barrier zone 90 such that the longitudinal edges of the topsheet 24 are disposed within the barrier zone 90 of the barrier cuff 60. In other embodiments, the topsheet may be wrapped around the longitudinal edges 29 of the core 28 such that the longitudinal edges of the topsheet 24 are disposed between the core 28 and the backsheet 26.

The leg elastic members 72 are shown as being disposed on the backsheet 26 and longitudinally outboard of the absorbent core 28. In other embodiments, the leg elastic members 72 may be disposed within the backsheet 26 (e.g., elastics are formed in the backsheet) or the leg elastic members 72 may be disposed between the layers that form the backsheet 26.

Another suitable embodiment for the contoured barrier cuff 60 is shown in the cross-sectional views of FIGS. 1E-F. FIGS. 1E-F are variants of the contoured barrier cuffs shown in FIGS. 1C-D. FIG. 1E represents a cross-section taken through the crotch point (i.e., the sectional line being the lateral centerline in FIG. 1A), and FIG. 1F represents a cross-section taken through front end region or the rear end region (sectional lines a-a and b-b of FIG. 1A). As shown in FIGS. 1E-F, the attachment zone 92 may extend laterally outboard of the longitudinal edge 29 of the core 28. Extending the attachment zone 92 laterally outboard of the longitudinal edge 29 of the core 28 may allow for a more secure bond to be placed between the topsheet 24, the barrier cuff 60, and the backsheet 26. In certain embodiments where the attachment zone 92 extends laterally outboard of the longitudinal edge 29 of the core 28, the transition edge 94 is likewise disposed laterally outboard of the longitudinal edge 29 of the core 28. In certain embodiments, the transition edge 94 may be less than about 3.0 cm from the longitudinal edge 29 of the core 28. In other embodiments, the transition edge 94 is less than 2.0 cm or 1.0 cm from the longitudinal edge 29 of the core 28. Minimizing the lateral distance of the transition edge 94 beyond longitudinal edge 29 of the core 28 reduces the likelihood that body exudates will channel away the core 28. By channeling away from the core 28, the exudates may not be absorbed by the core 28 and are prone to leak.

Figure 2C:
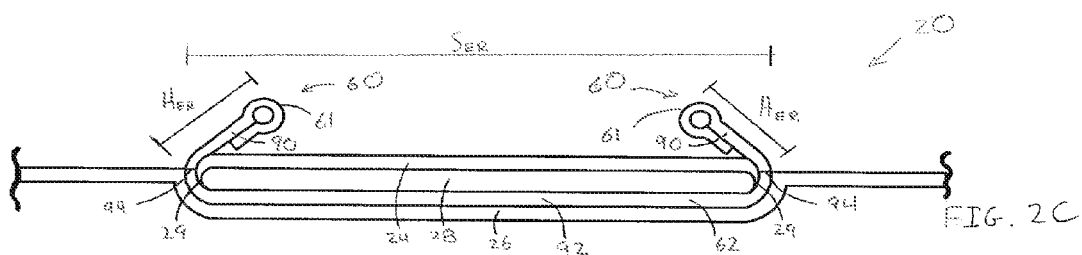
FIGS. 2B-C are cross-sectional views of the diaper of FIG. 2A taken when the diaper is fastened and ready for wear.
Figure 2B:
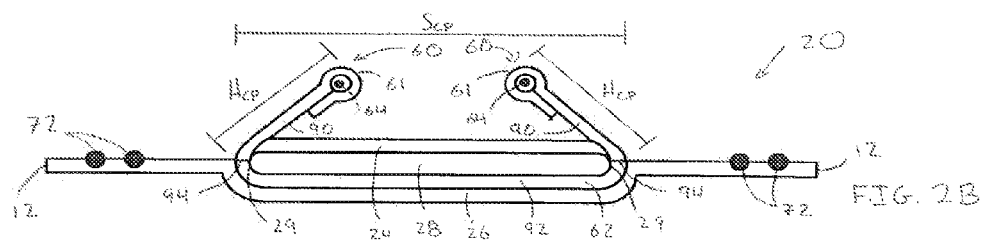

FIGS. 2A-C depict another suitable construction of an absorbent article having contoured barrier cuffs 60. A diaper having contoured barrier cuffs is shown in FIG. 2A in a flat, uncontracted state (i.e., without elastic induced contraction). FIGS. 2B-C are cross-sectional views of the diaper of FIG. 2A taken when the diaper is fastened (e.g., fastening system, if present, is engaged) and ready for wear (e.g., diaper forms two leg openings and a waist opening). FIG. 2B is a cross-section taken through the crotch point of the diaper (i.e., the sectional line being the lateral centerline in FIG. 2A). FIG. 2C is representative of a cross-section taken through either sectional line a-a in the front end region of the diaper 20 in FIG. 2A or sectional line b-b in the rear end region of the diaper 20 in FIG. 2A. This embodiment is a variation of that shown in FIG. 1C-D. Aside from the barrier cuff 60 construction as will be discussed, other elements and their construction remain similar to that presented above in regard to the diaper of FIGS. 1C-D.

In FIGS. 2A-C, the contoured barrier cuffs 60 are shown as being formed from a continuous barrier member 62. The use of a continuous barrier member 62 may result in improved containment since the cuff 60 itself forms a "U"-shaped cup within which body exudates may be deposited and contained. Furthermore, the use of a single continuous barrier member 62 to form the barrier cuffs 60 rather than two discrete members (as shown in the diaper of FIG. 1C-D) may yield cost savings and may reduce processing complexity.

The contoured barrier cuff 60 may comprise a spacing means such as spacing elastic members 64, which are shown disposed proximate to opposing longitudinal edges 61. As shown in FIGS. 2B-C, the barrier cuff 60 includes an attachment zone 92 which comprises at least the portion of the barrier member 62 disposed between the absorbent core 28 and the backsheet 26. The attachment zone 92 may be joined to the backsheet 26, the absorbent core 28, or both.

The barrier cuff 60 is shown extending away from the body-facing surface of the diaper 20 to form the barrier zone 90. The barrier zone 90 includes the opposing upstanding longitudinal edges 61 and the spacing elastic member 64. The transition edge 94 is shown separating the barrier zone 90 from the attachment zone 94. It should be appreciated that the transition edge 94 is the boundary between the barrier zone 90 and attachment 94. Although the transition edge 94 is shown as being a line through the barrier cuff 60, the line is symbolic and does not suggest the existence of a physical line in the diaper 20.

FIG. 2B shows the crotch point cuff height $H_{CP}$ and the crotch point span $S_{CP}$. FIG. 2C shows the end region cuff height $H_{ER}$ and the end region span $S_{ER}$. While FIGS. 2A-C are not to be taken as drawn to scale, one should appreciate that the crotch point cuff height $H_{CP}$ is greater than the end region cuff height $H_{ER}$. Furthermore, one should appreciate that the crotch point span $S_{CP}$ is less than end region span $S_{ER}$. Having the barrier cuff 60 disposed under the core 28 and wrapping about the longitudinal edges 29 of the core, the available barrier zone 90 changes to a degree that is approximately proportional to the width of the core 28. Specifically for this embodiment, the wider portions of the core 28 translate into cuffs having reduced height and wider span. Conversely, the narrower regions of the core 28 translate into cuffs having increased height and narrower span.

For this embodiment, the crotch point cuff height $H_{CP}$ may be 37 mm and the crotch point span $S_{CP}$ may be 70 mm. The end region cuff height $H_{ER}$ may be 17 mm and the end region span $S_{ER}$ may be 110 mm. However, specific dimensions may vary particularly when diapers 20 are produced on high speed machinery. The cuff height ratio is greater than 1. However, the cuff height ratio may be greater than 1.5, 2, 3, 4, 5, or 10. The cuff span ratio is greater than 1. However, the cuff span ratio may be greater than 1.25, 1.5, 1.75, or 2.

Another suitable embodiment for the contoured barrier cuff 60 is shown in the cross-sectional views of FIGS. 2D-E. FIGS. 2D-E are variants of the contoured barrier cuffs shown in FIGS. 2B-C. FIG. 2D represents a cross-section taken through the crotch point (i.e., the sectional line being the lateral centerline in FIG. 2A). FIG. 2E illustrates a cross-section taken through either sectional line a-a in the front end region of the diaper 20 in FIG. 2A or sectional line b-b in the rear end region of the diaper 20 in FIG. 2A. As shown in FIGS. 2D-E, the attachment zone 92 may extend laterally outboard of the longitudinal edge 29 of the core 28. Extending the attachment zone 92 laterally outboard of the longitudinal edge 29 of the core 28 may allow for a more secure bond to be placed between the topsheet 24, the barrier cuff 60, and the backsheet 26. In certain embodiments where the attachment zone 92 extends laterally outboard of the longitudinal edge 29 of the core 28, the transition edge 94 is likewise disposed laterally outboard of the longitudinal edge 29 of the core 28. In certain embodiments, the transition edge 94 may be less than about 3.0 cm from the longitudinal edge 29 of the core 28. In other embodiments, the transition edge is less than 2.0 cm or 1.0 cm from the longitudinal edge 29 of the core 28. Minimizing the lateral extension of the transition edge beyond longitudinal edge 29 of the core 28 reduces the likelihood that body exudates will channel away the core 28. By channeling away from the core 28, the exudates may not be absorbed by the core 28 and are prone to leak.

Figure 3A:
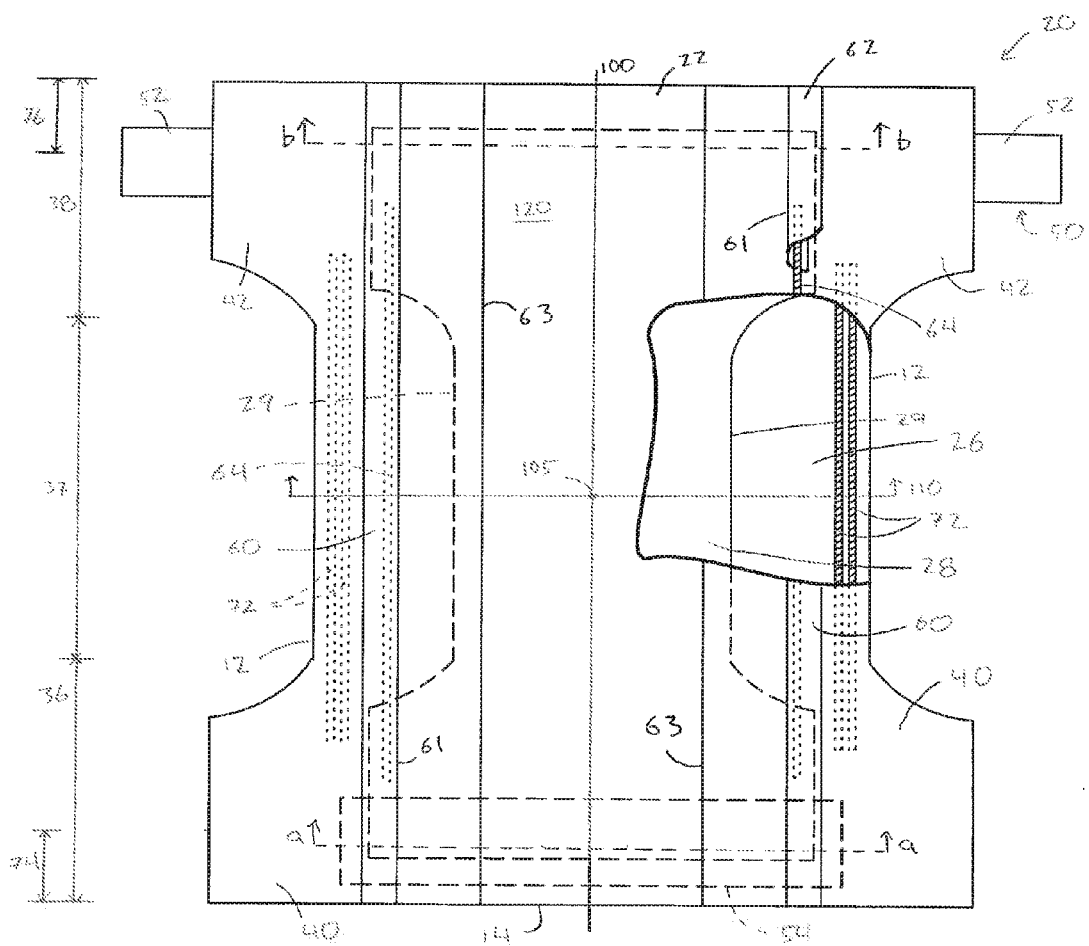
FIG. 3A is a plan view of a plan view of another embodiment of diaper having contoured barrier cuffs.
Figure 3C:
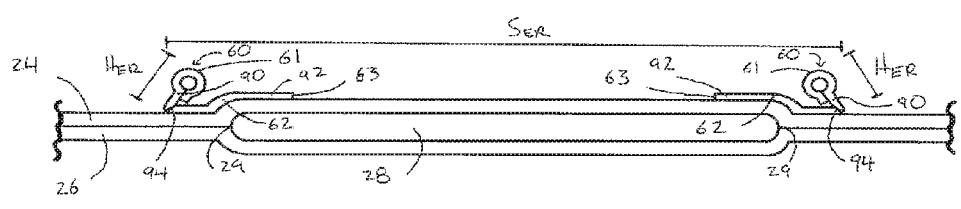
FIGS. 3B-C are cross-sectional views of the diaper of FIG. 3A taken when the diaper is fastened and ready for wear.
Figure 3B:
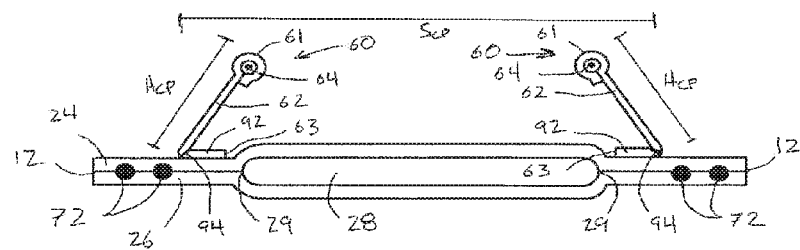
Figure 3D:
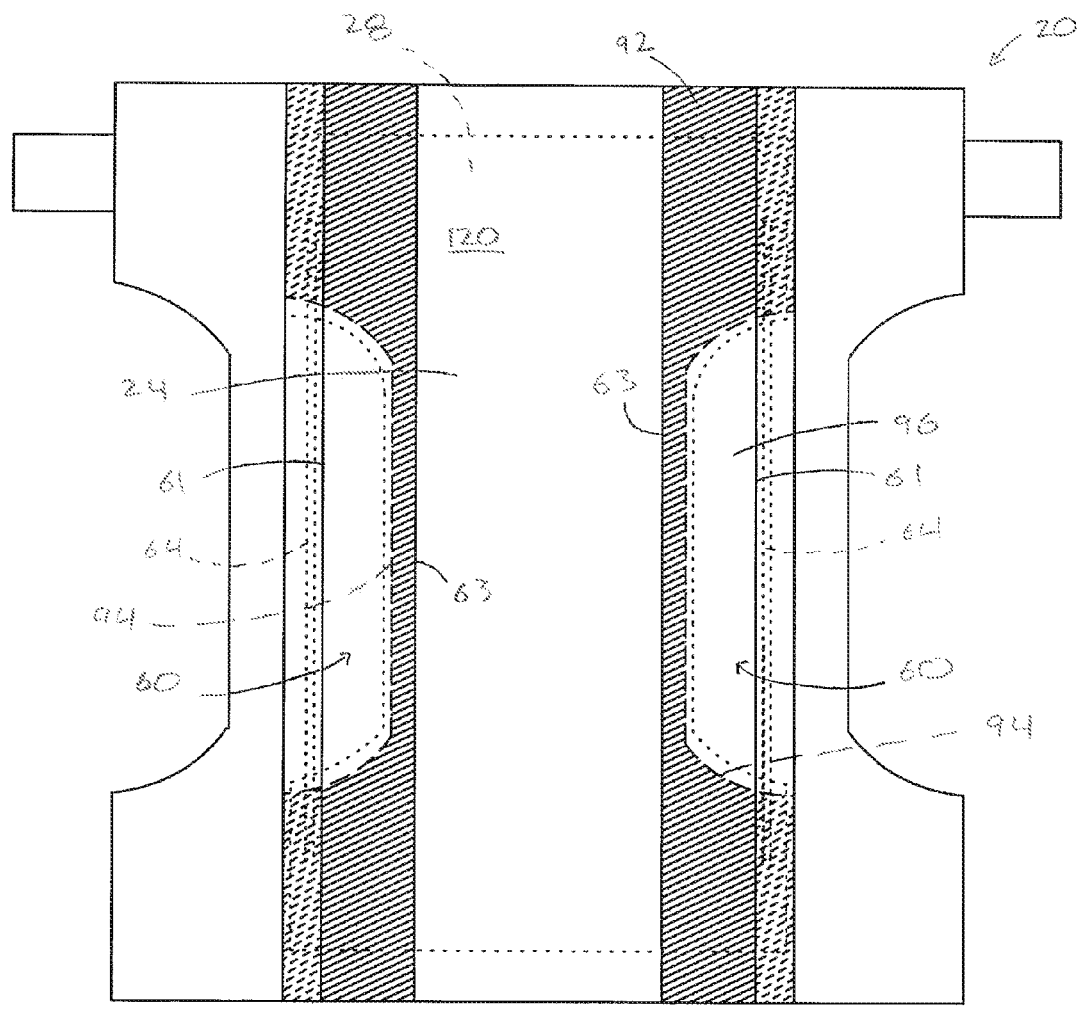
FIG. 3D is an alternate plan view of the diaper of FIG. 3A highlighting the attachment zone.

Another embodiment of a diaper having contoured barrier cuffs is shown in FIG. 3A in a flat, uncontracted state (i.e., without elastic induced contraction). FIGS. 3B-D are cross-sectional views of the diaper 20 taken when the diaper 20 is fastened (e.g., fastening system, if present, is engaged) and ready for wear (e.g., diaper forms two leg openings and a waist opening). FIG. 3B is a cross-section taken through the crotch point of the diaper (i.e., the sectional line being the lateral centerline in FIG. 3A). FIG. 3C is representative of a cross-section taken through either sectional line a-a in the front end region of the diaper 20 in FIG. 3A or sectional line b-b in the rear end region of the diaper 20 in FIG. 3A. In this embodiment, the contoured barrier cuffs 60 are shown as being disposed on the topsheet 24. Each barrier cuff 60 comprises a discrete barrier member 62 and a spacing elastic member 64. The attachment zone 92 of the barrier cuff 60 is generally the portion of the barrier member 62 joined to the topsheet 24 and prevented from lifting away from the body-facing surface of the diaper 20 during wear. The attachment zone 92 may be joined to the topsheet 24 in a manner such that a liquid impermeable barrier forms impeding the lateral flow or wicking of liquid. For example, the attachment zone 92 may be joined by a liquid impermeable adhesive that permeate the topsheet 24 or by mechanical bond that fuses the topsheet 25 and attachment zone 92 to form a film layer.

The barrier cuff 60 is shown extending away from the body-facing surface of the diaper 20 to form the barrier zone 90. The barrier zone 90 generally includes the upstanding edge 61 and the spacing elastic member 64. The transition edge 94 is shown separating the barrier zone 90 from the attachment zone 94. It should be appreciated that the transition edge 94 is the boundary between the barrier zone 90 and attachment zone 92. Although the transition edge 94 is shown as being a line through the barrier cuff 60, the line is symbolic and does not suggest the existence of a physical line in the diaper 20.

FIG. 3B shows the crotch point cuff height Hp and the crotch point span $S_{CP}$. FIG. 3C shows the end region cuff height $H_{ER}$ and the end region span $S_{ER}$. While FIGS. 3A-C are not to be taken as drawn to scale, one should appreciate that the crotch point cuff height $H_{CP}$ is greater than the end region cuff height $H_{ER}$. Furthermore, one should appreciate that the crotch point span $S_{CP}$ is less than end region span $S_{ER}$. The variable cuff height and cuff span exhibited by the contoured barrier cuff 60 of the present embodiment is achieved by shaping the attachment zone 92. The attachment zone 92 is laterally wider in either end region than through the crotch point. The increased width of the attachment zone 92 in the end region results in increased cuff span (i.e., the distance between the transition edges is increased) and decreased cuff height (i.e., the amount of barrier material 92 available to form the barrier zone 90 is reduced). In the narrower regions of the diaper 20 such as at the crotch point, the lateral width of the attachment zone 92 is minimized thereby decreasing cuff span and increasing cuff height. FIG. 3D is another plan view of the diaper 20. Unlike the view of FIG. 3A, several structures have been omitted from FIG. 31) in order to show the shape of the attachment zone 92 of the contoured barrier cuff 60. The attachment zone 92 is highlighted by hatch-marking. Because the attachment zone 92 is tapered laterally inward (i.e., toward the longitudinal centerline 100) in the crotch region 37 of the diaper 20, the barrier zone 90 has greater lateral width which translates into greater cuff height H. The pattern of the attachment zone 92 is exemplary. Other shapes and widths of the attachment zone 92 that yield a contoured barrier cuff having a contoured cuff height H and contoured cuff span S are within the scope of the present invention.

For the present embodiment, the crotch point cuff height $H_{CP}$ may be 37 mm and the crotch point span $S_{CP}$ may be 70 mm. The end region cuff height $H_{ER}$ may be 17 mm and the end region span $S_{ER}$ may be 110 mm. However, specific dimensions may vary particularly when diapers 20 are produced on high speed machinery. The cuff height ratio is greater than 1. However, the cuff height ratio may be greater than 1.5, 2, 3, 4, 5, or 10. The cuff span ratio is greater than 1. However, the cuff span ratio may be greater than 1.25, 1.5, 1.75, or 2.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any definition or meaning of a term in this written document conflicts with any definition or meaning of the term in a document incorporated by reference, the definition or meaning assigned to the term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a body-facing surface, garment-facing surface, a front waist region, a rear waist region, and a crotch region between the front and rear waist regions, said absorbent article comprising:
   a) a chassis, said chassis comprising a backsheet, a liquid permeable topsheet, and an absorbent core disposed between said backsheet and said topsheet, wherein said absorbent core has opposing longitudinal edges; and
   b) a pair of longitudinally disposed barrier cuffs each comprising a barrier zone, an attachment zone, and a transition edge separating the barrier zone and attachment zone, wherein said barrier cuff is joined to the chassis within the attachment zone and wherein said barrier zone comprises a longitudinally extending elastic member joined to a barrier member such that said elastic member lifts said barrier zone away from the body-facing surface of the absorbent article during wear of the absorbent article,
wherein each of said pair of barrier cuffs is formed at least in part of a layer of material that is partially disposed between said absorbent core and said backsheet
wherein said barrier cuffs exhibit a cuff height at a given cross-section through a crotch point and an end region, and wherein said absorbent article exhibits a cuff height ratio, defined as a cuff height as measured at the crotch point divided by a minimum cuff height as measured in the end region, of greater than 1.

2. The article of claim 1 wherein the transition edge is no further than about 1.0 cm laterally outboard of the nearest longitudinal edge of the absorbent core.

3. The article of claim 1 wherein the barrier cuffs are joined directly to the backsheet.

4. The article of claim 1 wherein the cuff height ratio is greater than 2.

5. The article of claim 1 wherein the barrier member is substantially rectilinear.

6. An absorbent article having a body-facing surface, garment-facing surface, a front waist region, a rear waist region, and a crotch region between the front and rear waist regions, said absorbent article comprising:
   a) a chassis, said chassis comprising a backsheet, a liquid permeable topsheet, and an absorbent core disposed between said backsheet and said topsheet, wherein said absorbent core has opposing longitudinal edges; and b) a pair of opposing longitudinally disposed barrier cuffs comprising:

i) a barrier member having an upstanding longitudinal edge; said barrier member disposed at least partially between the absorbent core and the backsheet, said barrier member extending laterally beyond the longitudinal edge of the absorbent core, and ii) a longitudinally extending elastic member joined to the barrier member in proximity to the upstanding longitudinal edge such that said elastic member lifts a portion of the barrier member away from the body-facing surface of absorbent article during wear of the absorbent article;

wherein each barrier cuff has a barrier zone, an attachment zone, and a transition edge separating the barrier zone and attachment zone; wherein said barrier cuffs exhibit a cuff height at a given cross-section through a crotch point and an end region, wherein each of said barrier cuffs is formed at least in part of a layer of material that is partially disposed between said absorbent core and said backsheet;

wherein said topsheet is disposed laterally between the opposing barrier cuffs, and wherein said absorbent article exhibits a cuff height ratio, defined as a cuff height as measured at the crotch point divided by a minimum cuff height as measured in the end region, of greater than 1.

7. The article of claim 6 wherein the transition edge is disposed no further than about 3.0 cm laterally outboard of the nearest longitudinal edge of the absorbent core.

8. The article of claim 6 wherein the attachment line is no further than about 1.0 cm laterally outboard of the nearest longitudinal edge of the absorbent core.

9. The article of claim 6 wherein the barrier member comprising the barrier cuff is a discrete barrier member.

10. The article of claim 6 wherein the barrier member is a continuous barrier member whereby the barrier cuffs comprise the same continuous barrier member.

11. The article of claim 6 wherein the cuff height ratio is greater than 2.

12. The article of claim 6 wherein the barrier member is substantially rectilinear.

13. An absorbent article having a body-facing surface, garment-facing surface, a front waist region, a rear waist region, and a crotch region between the front and rear waist regions, said absorbent article comprising:

a) a chassis, said chassis comprising a backsheet, a liquid permeable topsheet, and an absorbent core disposed between said backsheet and said topsheet; and b) a pair of opposing longitudinally disposed barrier cuffs comprising:

i) a barrier member having an upstanding longitudinal edge and a proximal longitudinal edge; said proximal longitudinal edge being joined to the topsheet, and ii) a longitudinally extending elastic member joined to the barrier member in proximity to the upstanding longitudinal edge such that said elastic member lifts a portion of the barrier member away from the topsheet during wear of the absorbent article;

wherein each barrier cuff has an attachment zone, which is a portion of the barrier cuff joined to the topsheet; a barrier zone, which is a portion of the barrier cuff the lifts away from the topsheet during wear of the absorbent article; and a transition edge separating the barrier zone and attachment zone; wherein said barrier cuffs exhibit a cuff height at a given cross-section through a crotch point and an end region, wherein each of said pair of barrier cuffs is formed at least in part of a layer of material that is partially disposed between said absorbent core and said backsheet; and wherein said absorbent article exhibits a cuff height ratio, defined as a cuff height as measured at the crotch point divided by a minimum cuff height as measured in the end region, of greater than 1.

14. The article of claim 13 wherein the cuff height ratio is greater than 2.

15. The article of claim 13 wherein the barrier member is substantially rectilinear.

\* \* \* \* \*